(12) United States Patent
Sennett

(10) Patent No.: US 6,641,613 B2
(45) Date of Patent: Nov. 4, 2003

(54) DOUBLE DOWEL SPINAL FUSION IMPLANT

(75) Inventor: Andrew R. Sennett, Hanover, MA (US)

(73) Assignee: Cortek, Inc., Dedham, MA (US)

( * ) Notice: Subject to any disclaimer, the term of this patent is extended or adjusted under 35 U.S.C. 154(b) by 0 days.

(21) Appl. No.: 10/060,740

(22) Filed: Jan. 30, 2002

(65) Prior Publication Data

US 2003/0144736 A1 Jul. 31, 2003

(51) Int. Cl.[7] ................................................. A61F 2/44
(52) U.S. Cl. ................................................... 623/17.11
(58) Field of Search ........................ 623/17.11, 17.12, 623/17.13, 17.14, 17.15, 17.16; 606/61, 60, 72, 73

(56) References Cited

U.S. PATENT DOCUMENTS

| 6,149,686 | A | * | 11/2000 | Kuslich et al. | .......... 623/17.11 |
| 6,206,922 | B1 | * | 3/2001 | Zdeblick et al. | .......... 623/17.11 |
| 6,224,631 | B1 | * | 5/2001 | Kohrs | .......... 623/17.11 |
| 6,391,058 | B1 | * | 5/2002 | Kuslich et al. | .......... 623/17.11 |
| 6,402,785 | B1 | * | 6/2002 | Zdeblick et al. | .......... 623/17.16 |
| 6,419,706 | B1 | * | 7/2002 | Graf | .......... 623/17.16 |
| 6,485,517 | B1 | * | 11/2002 | Michelson | .......... 623/17.11 |
| 6,547,823 | B2 | * | 4/2003 | Scarborough et al. | ... 623/17.16 |

* cited by examiner

Primary Examiner—David J. Isabella
(74) Attorney, Agent, or Firm—Burns & Levinson LLP; Frederick C. Williams; Yan Lan

(57) ABSTRACT

The invention is a unitary implant or graft made of allograft bone or of similar material and shaped as a conjoined double dowel. Six embodiments of the implant are shown along with three embodiments for a vertebral distractor and reamer guide.

6 Claims, 6 Drawing Sheets

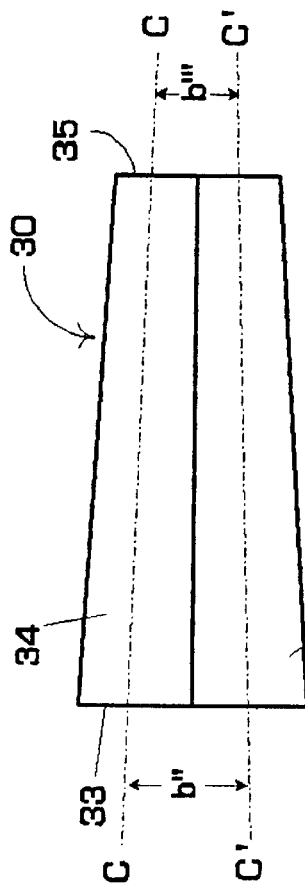
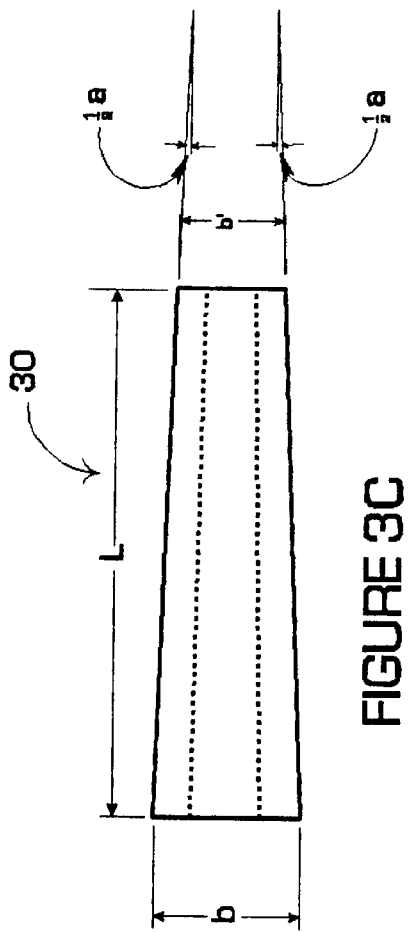
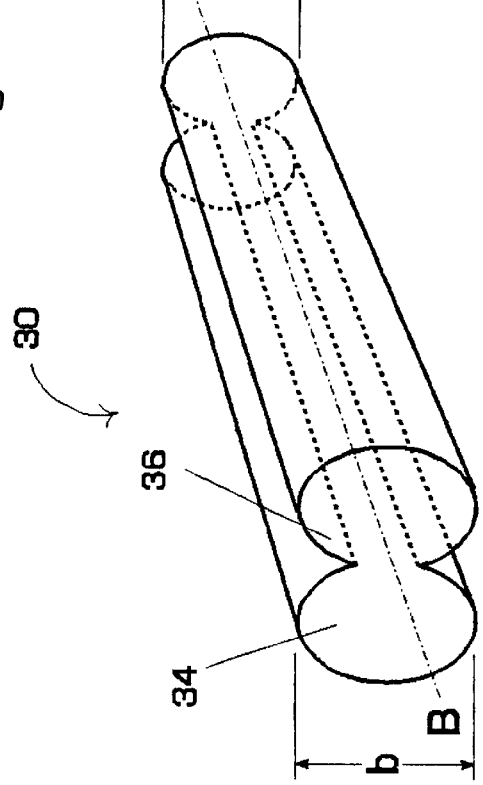

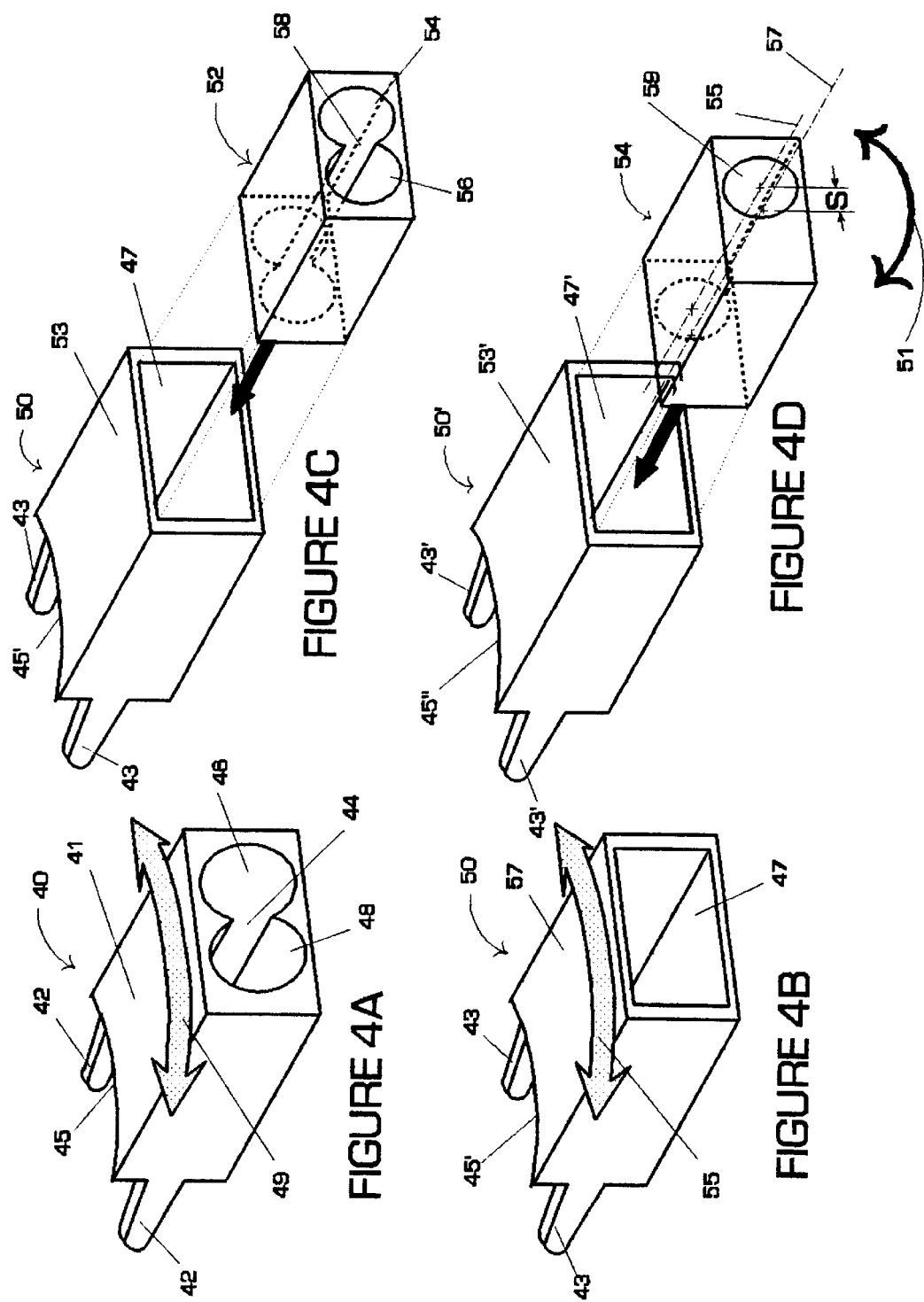

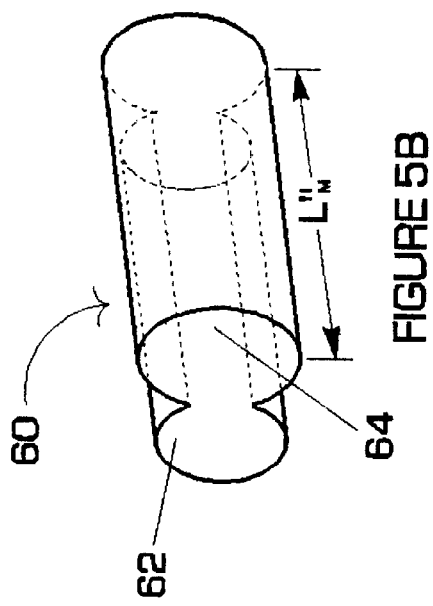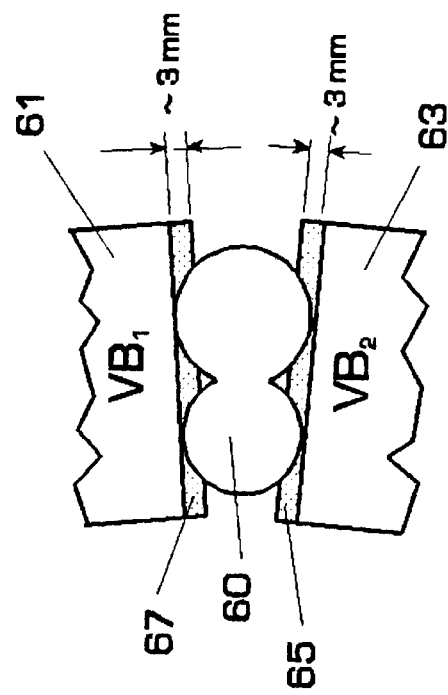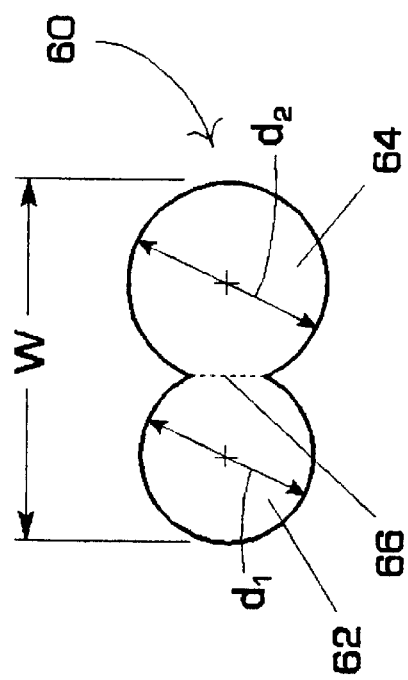

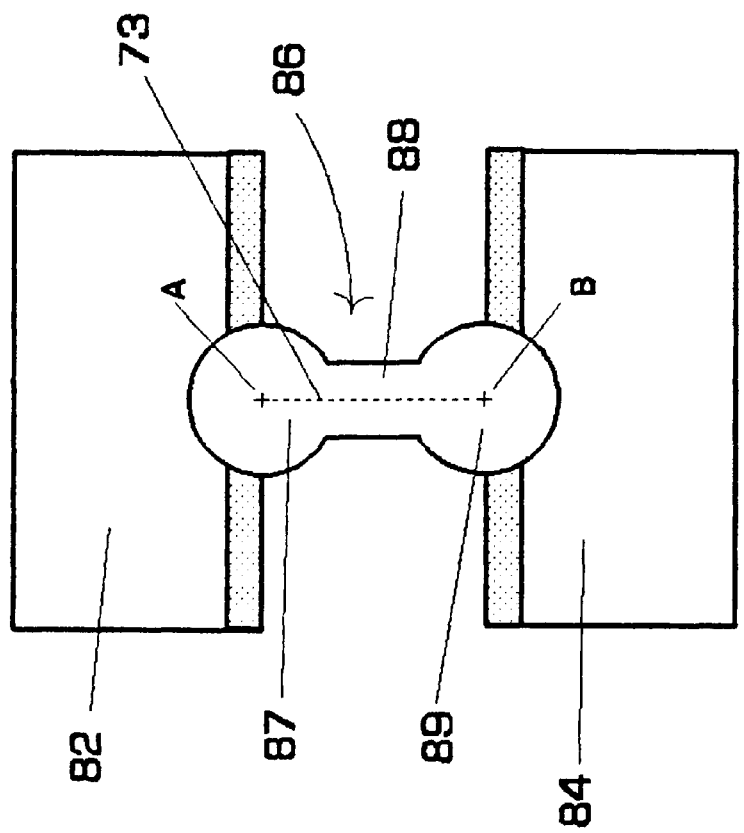
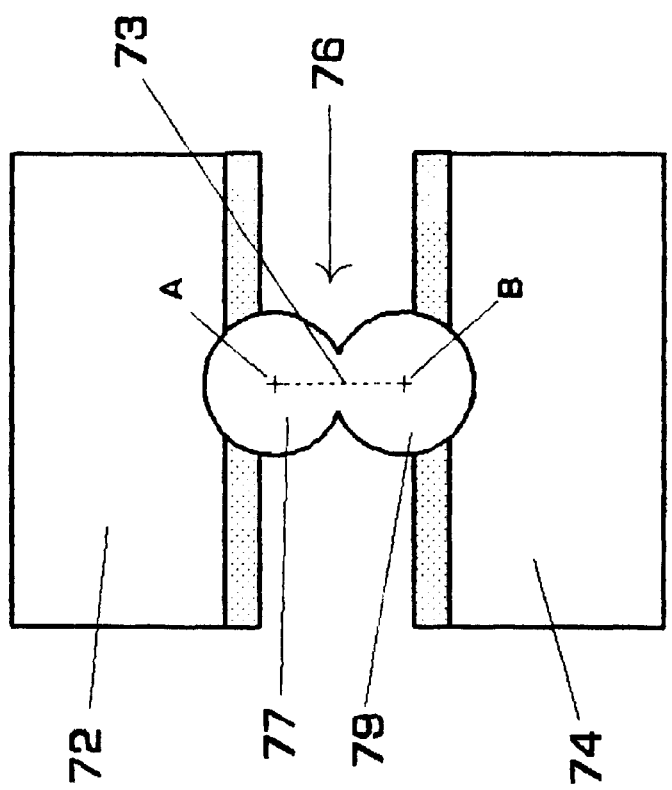

DOUBLE DOWEL SPINAL FUSION IMPLANT

FIELD OF INVENTION

This invention relates generally to the treatment of injured, degenerated, or diseased tissue in the human spine, especially failed intervertebral discs and diseased vertebrae. It further relates to the removal of damaged tissue and to the stabilization of the remaining spine by bony fusion of at least two vertebrae adjacent or nearly adjacent to the space left by the surgical removal of tissue. More particularly, this invention relates to the implantation of devices which can structurally replace the removed discs during healing and at the same time share compressive load to facilitate growth of new bone between adjacent vertebrae. This invention further relates to the implantation of devices which are compatible with the natural curvature of the spinal column.

BACKGROUND OF THE INVENTION

For many years a treatment, often a treatment of last resort, for serious back problems has been spinal fusion surgery. Disc surgery, for example, typically requires removal of a portion or the entirety of an intervertebral disc. In such cases the structural contribution of the removed disc must be replaced. The most common sites for such surgery, namely those locations where body weight most concentrates its load, are the lumbar discs in the L1-2, L2-3, L3-4, L4-5, and L5-S1 intervertebral spaces. In addition, a number of degenerative diseases and other conditions such as scoliosis require correction of the relative orientation of vertebrae by surgery and fusion.

In current practice, a surgeon will use one or more procedures known in the art to attempt to fuse remaining adjacent spinal vertebrae. Some of the prior art techniques used with at best mixed success have been described in Nicholson, et al., U.S. Pat. No. 6,096,080, issued Aug. 1, 2000, which is incorporated by reference as though fully set forth herein. That patent set forth a successful advance over such prior art.

Prior art methods of attempting to achieve fusion as described in Nicholson, et al. do not produce reliable and predictable results. For example, Fraser, R. D. points out in "Interbody, Posterior and Combined Fusions," Spine, V20 (24S):1675, Dec. 15, 1995: "[A]nalysis of the literature does not indicate that one form of fusion is significantly better than another for degenerative conditions of the lumbar spine." Ray, Charles D., reported the results of the original IDE study involving his Ray Threaded Fusion Cage (Ray-TFC) in Spine V22(6):667, Mar. 15, 1997. The study reported that of the two hundred eight patients who had two year follow-up, 96% had fusion but with only 40% having excellent results and 25% having fair or poor results.

There is a strong current of opinion among leading spine surgeons that loading the material which is to become bone and produce fusion with a compressive mechanical load yields superior results both in strength and in brevity of healing time. Such loading works in conjunction with the standard procedure of preparing the vertebrae to be fused by breaking through, or cutting into, the hardened endplate surfaces of vertebral bone so as to allow an interposed bone graft or implant to come into direct contact with vascularized cancellous bone tissue. The latter enables blood flow through material placed in the intervertebral space which in turn initiates the growth of new bone across the intervertebral space. This process allows for the incorporation of inserted bone grafts or implants into the two respective adjacent vertebral surfaces such that they become one continuous and rigid segment of bone.

In addition, the restoration of normal anatomy is a basic principle of all orthopedic reconstructive surgery. Lordosis, a pronounced forward curvature of the lumbar region of the spine, is a factor relevant to the design of lumbar implants. It is known in the art that the preservation of the natural curvature of the lumbar spine requires a design having a modest taper approximately equivalent to the effective angularity of the removed tissue.

Therefore there is a perceived need for a device which simultaneously provides: mechanical stability upon implantation; a proper substrate such as allograft bone to induce the growth of bone across the implant region; compressive loading to the implant so as to enhance bone growth and calcification; and accommodation to the normal anatomical curvature of the spine. There is also a perceived need for an implant configuration that can be used in other regions of the spine in addition to the lumbar region, specifically in the cervical region.

Bone based implants may have cylindrical, rectangular, and generic shapes. In the past, Cloward, Wilterberger, Crock, Viche, Bagby, Brantigan, and others have taught various methods involving the drilling of holes across the disc space between two adjacent vertebrae of the spine for the purpose of causing an interbody spinal fusion upon placement of a dowel in the hole. Cloward, for instance, taught placing a dowel of bone within a drilled hole for the purpose of bridging the intervertebral gap and incorporating the dowel into the fusion. Viche taught the threading of that bone dowel.

Bone used in dowel implants can be obtained from the patient's own hip iliac crest or it can be obtained as allograft from a tissue processor such as Regeneration Technologies, Inc. Many prior art bone grafts required distraction of the intervertebral space and contouring of the bone graft to ride on the end plates of the vertebral bodies.

Dowel bone grafts have been described in, for example, the following U.S. Patents: Michelson in U.S. Pat. Nos. 5,015,247, 5,860,973, and 6,149,650; Grivas, et al., in U.S. Pat. No. 5,814,084; Zdeblick, et al., in U.S. Pat. Nos. 6,206,922 and 6,245,072; Koros in U.S. Pat. No. 6,217,579; and McKay in U.S. Pat. No. 6,261,586.

Michelson, in U.S. Pat. No. 5,015,247 (May 14, 1991), describes a "threaded spinal implant" which would plausibly be a dowel type design with threads. Grivas, et al., in U.S. Pat. No. 5,814,084 (Sep. 29, 1998), describe a dowel made from "a plug from the shaft (diaphysis) of various long bones." Grivas et al. state that their dowel has improved biomechanical and vertebral fusion induction properties compared to standard dowels known in the art.

Michelson, in a later patent, U.S. Pat. No. 5,860,973 (Jan. 19, 1999), teaches a spinal implant design which is "at least in part cylindrical in shape." However, the use of a single dowel bone graft implant tends to flatten the intervertebral space, causing it to be distracted in such a way as to induce an undesirable change in spinal curvature. Also, the instrumentation used to implant single dowels is bulky and tends to be difficult to use partly because it blocks direct view of the implantation site. The Cloward method is now mostly of historical interest and has been largely replaced by methods such as the Smith-Robinson technique in which a straightforward discectomy is followed by implantation of a square block of bone. Smith-Robinson has been until recently a standard, even though it has problems related to both (1)

bone non-incorporation, mostly due to poorly interfaced surfaces since the end plate of the vertebral bodies is not a square configuration, and (2) collapse or telescoping of the graft within the patient's adjacent vertebral body causing pain. Such complications may be attributed to poor fit of the graft and inadequate preparation of the endplates to accept the graft.

The invention of Nicholson, et al., U.S. Pat. No. 6,096,080 made great strides in overcoming the many disadvantages of prior art devices and procedures. However, it nevertheless had some drawbacks which are addressed by the current invention. The dovetail implant of that invention can only be placed in one orientation if it is to achieve its full intended effect. Moreover, it requires a relatively wide distraction of the adjacent vertebrae to accommodate the height of the implant necessitated by the geometry of the dovetail configuration.

It is therefore an object of the current invention to provide a spinal fusion implant able to provide a substrate suitable to the induction of new bone growth between the vertebral bodies being fused. It is a further object to provide a device which promotes bone growth between vertebrae adjacent to the space left by the excised material by progressive sharing of the compressive load to the bone graft inserted within the device. It is a further object to create an implantable device for stabilizing the spine by limiting relative motion between the involved vertebrae in torsion loading during healing. It is yet a further object to provide mechanical stability between adjacent vertebrae while bone grows across the intervertebral space and while simultaneously maintaining the natural lordosis of the cervical or lumbar spine. It is a further object of the invention to provide a device which avoids or minimizes interference with various imaging technologies. It is yet another object of this invention to be capable of being fabricated from human bone allograft material. It is yet a further object of this invention to provide an implant which can be inserted with varying orientation. It is yet another object of this invention to provide an implant which provides interlocking capability but with a variable separation between the interlocking portions to allow for lesser distraction of adjacent vertebrae where such diminished distraction is necessary. It is yet another object of the invention to provide an implant which is also useful in the repair of cervical intervertebral defects.

SUMMARY OF INVENTION

The present invention is a design, in six embodiments, for a double dowel configuration of an intervertebral graft implant made of bone, preferably allograft bone, for use in the fusion of adjacent vertebral bodies. It further comprises three embodiments of a vertebral distractor and reamer guide intended for use in the preparation of the implantation site.

In its simplest form, the invention is a bone graft implant having a unitized shape of two conjoined circular cylindrical dowels whose major axes are laterally spaced apart by a distance that is less than half the sum of the diameters of the two circular cylindrical dowels at all points along the major length of the implant. The major axes of the conjoined circular cylindrical dowels are coplanar, and in this simplest embodiment the diameters of the two conjoined circular cylindrical dowels are equal. For cervical implantation, the diameter of each conjoined circular cylindrical dowel is between about 7 millimeters and about 14 millimeters. For lumbar implantation, the diameter of each conjoined circular cylindrical dowel is between about 10 millimeters and about 22 millimeters. When implanted, the plane in which the dowels are coplanar is perpendicular to the sagittal plane of the patient's spine.

A second embodiment of the double dowel design is characterized by a unitized shape of two conjoined circular cylindrical dowels whose major axes are laterally spaced apart by a distance that is less than half the sum of the diameters of the two circular cylindrical dowels at all points along the major length of the implant. The major axes of the conjoined circular cylindrical dowels are coplanar, and each double dowel set has a lordotic taper cut at one end. The diameters of the two conjoined circular cylindrical dowels are equal. For cervical implantation, the diameter of each conjoined circular cylindrical dowel is between about 7 millimeters and about 14 millimeters. For lumbar implantation, the diameter of each conjoined circular cylindrical dowel is between about 10 millimeters and about 22 millimeters. When implanted, the plane in which the dowels are coplanar is perpendicular to the sagittal plane of the patient's spine.

A third embodiment of the double dowel design is characterized by a unitized shape of two conjoined truncated conical dowels whose major conical axes are laterally spaced apart at all points along the length of the major dimension of the implant by a distance that is less than half the sum of the diameters of the two truncated conical dowels at all points along the length of the major dimension of the implant. The major axes of the conjoined truncated conical dowels are coplanar. The diameters of the two conjoined truncated conical dowels are equal at all points along the length of the major dimension of the implant. For cervical implantation, the major base diameter of each conjoined truncated conical dowel is between about 7 millimeters to about 14 millimeters. For lumbar implantation, the major base diameter of each conjoined truncated conical dowel is between about 10 millimeters to about 22 millimeters. When implanted, the plane in which the dowels are coplanar is perpendicular to the sagittal plane of the patient's spine.

In a fourth embodiment, the double dowels are circular cylinders having unequal diameters. When implanted, the plane in which the dowels are coplanar is closer to being perpendicular to the sagittal plane of the patient's spine than parallel to the sagittal plane.

In a fifth embodiment of the double dowel design is characterized by a unitized shape of two conjoined circular cylindrical dowels whose major axes are laterally spaced apart by a distance that is less than half the sum of the diameters of the two circular cylindrical dowels at all points along the major length of the implant. The major axes of the conjoined circular cylindrical dowels are coplanar, and the diameters of the two conjoined circular cylindrical dowels are equal. For cervical implantation, the diameter of each conjoined circular cylindrical dowel is between about 7 millimeters and about 14 millimeters. For lumbar implantation, the diameter of each conjoined circular cylindrical dowel is between about 10 millimeters and about 22 millimeters. When implanted, the plane in which the dowels are coplanar is parallel to the sagittal plane of the patient's spine.

In a sixth embodiment of the double dowel design is characterized by a unitized shape of two circular cylindrical dowels conjoined by an intervening planar bridge. The major axes of the conjoined circular cylindrical dowels are coplanar, and the diameters of the two conjoined circular cylindrical dowels are equal. For cervical implantation, the diameter of each conjoined circular cylindrical dowel is between about 7 millimeters and about 14 millimeters. For lumbar implantation, the diameter of each conjoined circular cylindrical dowel is between about 10 millimeters and about 22 millimeters. When implanted, the plane in which the dowels are coplanar is parallel to the sagittal plane of the patient's spine.

A first embodiment of the vertebral distractor for separating and maintaining separation of two adjacent vertebral bodies has two tapers disposed in lateral separation from one another and having a cavity comprised of two parallel and overlapping circular cylindrical bores penetrate the main body therethrough. The distractor has a curved land having a radius of curvature approximately equal to the radius of curvature of the anterior faces of vertebral bodies.

A second embodiment of the vertebral distractor used for separating and maintaining separation of two adjacent vertebral bodies has two portions, one of which is an outer body having a rectangular hole and two tapers disposed in lateral separation from one another, and a curved land having a radius of curvature approximately equal to the radius of curvature of the anterior faces of vertebral bodies. The other portion is an insertable reamer guide consisting of a rectangular solid having within itself two parallel and overlapping circular cylindrical bores comprising a single hole such that the overlapping circular cylindrical holes have axes that are separated by less than the diameter of either circular cylindrical hole with the axes of the two holes being disposed symmetrically within the two faces of the rectangular solid to which the axes of the holes are perpendicular.

A third embodiment of the vertebral distractor used for separating and maintaining separation of two adjacent vertebral bodies has two portions, one of which an outer body having a rectangular hole. It has two tapers disposed in lateral separation from one another and a curved land having a radius of curvature approximately equal to the radius of curvature of the anterior faces of vertebral bodies. The other portion is an insertable reamer guide consisting of a rectangular solid having within itself a cylindrical hole with an axis that is perpendicular to two rectangular faces of the rectangular solid and parallel to the four other rectangular faces of the rectangular solid and located such that the axis of the hole is separate from an axis is defined by a line passing between respective centroids of the two rectangular faces to which the axis is perpendicular with the separation between the axis of the hole and the axis being less than the radius of the hole.

BRIEF DESCRIPTION OF THE DRAWINGS

FIG. 3A is an oblique view of a third embodiment of the spinal implant of the present invention;

FIG. 3B is a first orthogonal view of a third embodiment of the spinal implant of the present invention;

FIG. 3C is a second orthogonal view of a second embodiment of the spinal implant of the present invention;

FIG. 4A is an oblique view of one embodiment of the vertebral distractor and reaming guide;

FIG. 4B is an oblique view of an alternative vertebral distractor;

FIG. 4C is an oblique view of the alternative vertebral distractor with one embodiment of an insertable reamer guide portion;

FIG. 4D is an oblique view of the alternative vertebral distractor with a second embodiment of an insertable reamer guide portion;

FIG. 5A is an end view of a dowel embodiment in which each dowel has a different diameter;

FIG. 5B is an oblique view of the double dowel embodiment of FIG. 5A;

FIG. 5C is an end-on view of double-dowel embodiment in place between two vertebral bodies;

FIG. 6A is a simplified orthogonal schematic anterior view of a fifth double dowel embodiment; and FIG. 6B is a simplified orthogonal schematic anterior view of a sixth double dowel embodiment.

TERMINOLOGY LINKING THE FIGURES TO THE DESCRIPTION

Figure 1B:
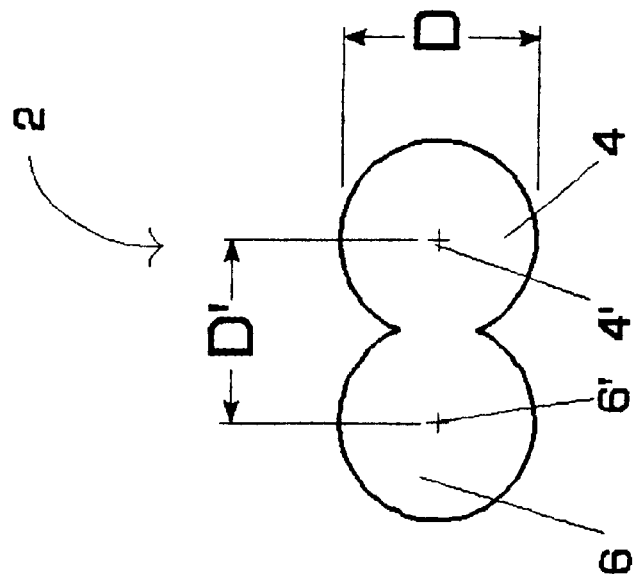
FIG. 1B is an end-on view of the embodiment shown in FIG. 1A.
Figure 1A:
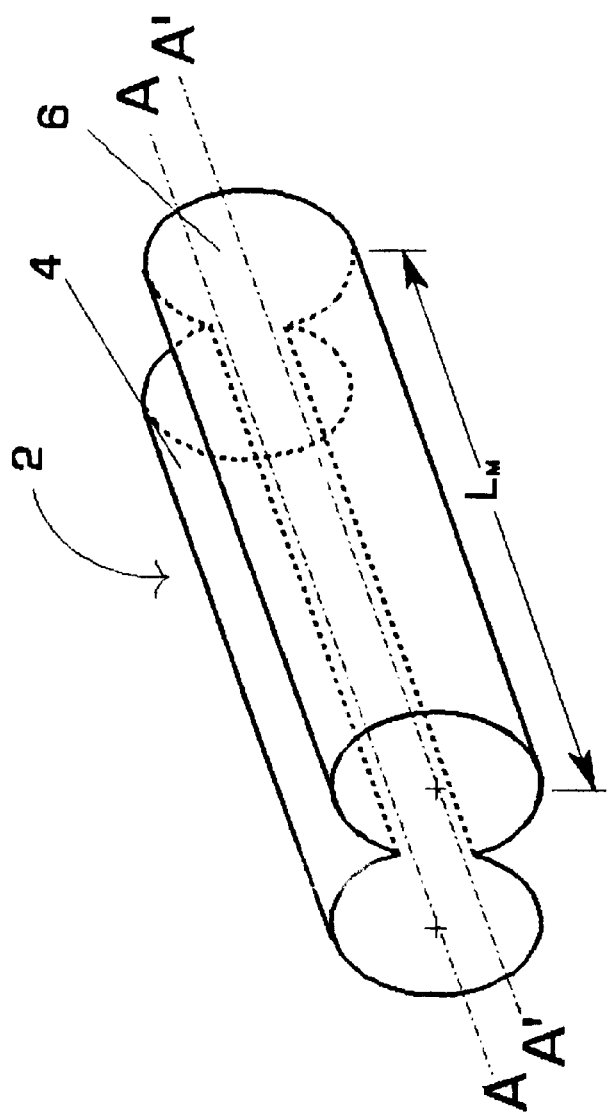
FIG. 1A is an oblique view of one embodiment of the spinal implant according to the present invention.

FIG. 1A
2—bone graft
4—conjoined circular cylinder
6—conjoined circular cylinder FIG. 1B
2—bone graft
4—conjoined circular cylinder
4'—axis of 4
6—conjoined circular cylinder
6'—axis of 6

Figure 2C:
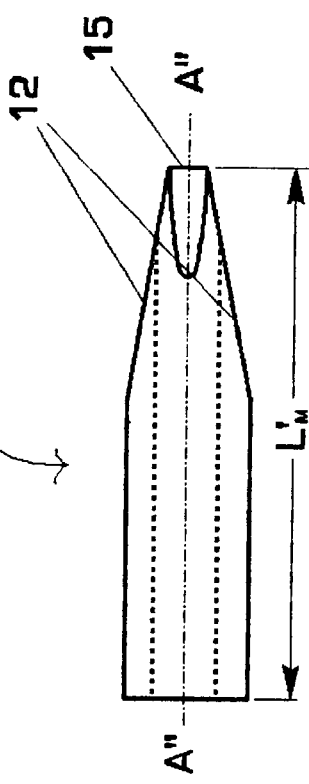
FIG. 2C is a second orthogonal view of a second embodiment of the spinal implant of the present invention.
Figure 2B:
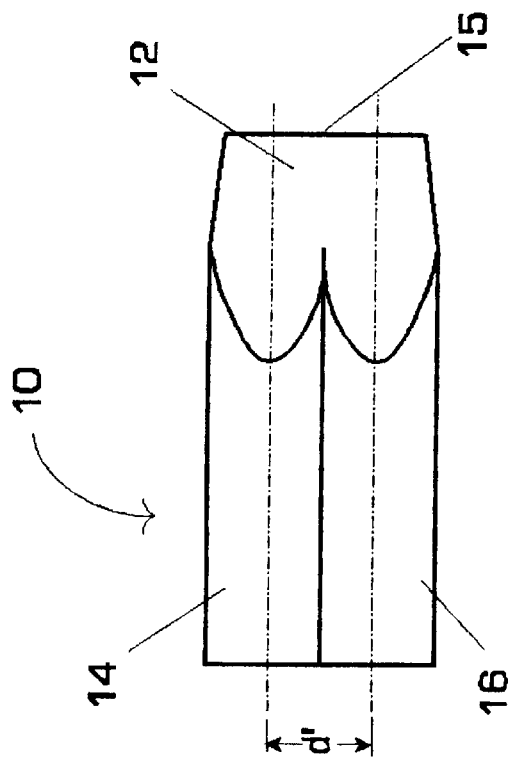
FIG. 2B is a first orthogonal view of a second embodiment of the spinal implant of the present invention.
Figure 2A:
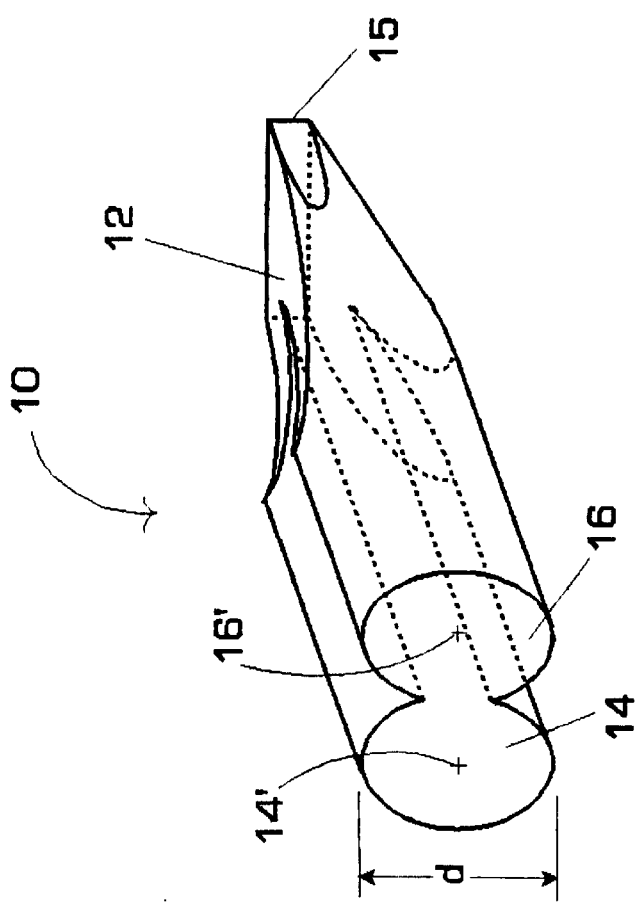
FIG. 2A is an oblique view of a second embodiment of the spinal implant of the present invention.

FIG. 2A
2—bone graft
12—face of taper
14—conjoined circular cylinder
15—lordotic tapered portion
16—conjoined circular cylinder FIG. 3A
30—bone graft
33—one end of graft
34—conjoined circular cone
35—one end of graft
36—conjoined circular cone FIG. 4A
40—vertebral distractor tool
41—main body of distractor
42—lordotic tapers
44—cavity in distractor
45—curved land
46,48—parallel and overlapping bores
49—two-headed arrow FIG. 4B
50—combined vertebral distractor tool and reamer guide box
43—lordotic tapers
45'—curved land
47—rectangular cavity
55—two-headed arrow
57—main distractor body FIG. 4C
43—lordotic tapers
45'—curved land
47—rectangular cavity
52—insertable reamer guide tool
53—main body of distractor
54,56—two parallel and overlapping circular cylindrical bores
58—noncircular cylindrical hole FIG. 4D
43'—lordotic tapers
45"—curved land
47'—rectangular cavity
51—double headed arrow
53'—main body of distractor
54—insertable reamer guide tool
55—axis if circular hole 59
57—centroidal axis of rectangular body
59—circular cylindrical hole FIG. 5A
60—fourth embodiment
62,64—cylindrical dowels having respective diameters $d_1$ and $d_2$
66—region of conjoining of double dowels 62,64

FIG. 5B
60—fourth embodiment
62,64—cylindrical dowels having respective diameters $d_1$ and $d_2$
66—region of conjoining of double dowels 62,64

FIG. 5C
60—fourth embodiment
61,63—upper and lower vertebral bodies
65,67—endplates of vertebral bodies 61,63

FIG. 6A
72—upper vertebral body
73—plane defined by major axes of dowels
74—lower vertebral body
76—bone graft implant
77—upper dowel portion of graft
79—lower dowel portion of graft FIG. 6B
82—upper vertebral body
83—plane defined by major axes of dowels
84—lower vertebral body
86—bone graft implant
87—upper dowel portion of graft
88—planar bridge between dowels
89—lower dowel portion of graft

DESCRIPTION OF THE PREFERRED EMBODIMENTS

Threaded metal cages, ordinary bone dowels and threaded bone dowels placed by anterior approach are often placed side by side in the disc space. The use of two such implants. or grafts, placed side-by-side improves stability and strength when compared to the use of a single dowel implant placed in the disc space on the midline. However, it is difficult and sometimes impossible to place adjacent dowels if the dowel diameters are greater than about 18 millimeters. The limitation is retraction of major vessels and the iliolumbar vein to expose the midline of the disc so as to gain access to the intervertebral disc space.

The present invention describes conjoined double dowel implant or graft designs which offer the potential to an improve fit within a tall disc space and the post-operative stability of the adjacent vertebral bodies being fused. With respect to terminology, the term "double dowel" does not mean two separate dowels but rather describes a unitary device which, in geometric terms, comprises the mathematical union of two dowel shapes, in one set of configurations, two cylindrical shapes fused together, in another configuration, two conical frustums fused together. In other variations of this invention, "double dowel" means two cylinders or two conical frustums, the center lines of which are separated by more that the sum of the radii of the two, and which are joined by a structural bridge or connector between them. For a double dowel in which the diameter of each dowel is X, the overall width of the joined double-dowel graft design according to the present invention is less than 2x. Therefore, a dowel diameter of 22 millimeters (mm), which is the size required to fit a tall lumbar disc, i.e., a large intervertebral space, can be achieved with an overall ideal width of 30 to 34 mm. A 22 mm threaded metal cage or bone dowel requires a minimum of 45 mm lateral width for implantation which cannot be achieved in most patients.

The same principle can be applied to the cervical spine. A double dowel can provide greater vertebral body coverage and greater strength and stability than a single dowel of the Cloward type, for example.

The graft designs described herein can be cut from the femoral head or vertebral body of donor bone. The graft can have parallel upper and lower surfaces, or it can include a lordotic taper. The lordotic taper can be fabricated by a second cutting operation during the manufacturing process.

Conventional disc reamers facilitate the preparation of the disc space. The reamer guide can be incorporated into the disc distractor tool. The distractor tip has a lordotic taper to correspond to the disc space when the tapers are inserted between the vertebral bodies being fused. The distractor body has a land that contacts the anterior margin of the adjacent vertebral bodies being fused. The body of the reamer guide also has two guide holes to accept the reamer, or it can be an insertable single bore reamer guide that can be inserted into a distractor designed as described hereinbelow for the purpose of reaming a first intervertebral region before the insertable guide is removed and then inverted 180 degrees and reinserted to accept a reamer guide that will prepare the remaining portion of the vertebral space. The handle of the distractor is oriented in a manner that does not interfere with the reaming axis.

Unitized Conjoined Double Dowel Graft—Graft Embodiment No.1

Referring to FIG. 1A there is shown in oblique view a vertebral implant or graft 2 made of donor bone for use in the fusion of adjacent vertebral bodies. The graft has the unitized shape of two conjoined circular cylinders 4 and 6 having equal diameter. The major length of the graft is defined in FIG. 1A as $L_M$. The axes A-A and A'-A' of each of the conjoined cylindrical dowels of the unitized double dowel are parallel one another and separated by a distance D' that is less than the diameter D of either cylinder, and they lie in the same plane. The specific geometry of the axis separation is evident in FIG. 1B where the double dowel arrangement of the implant 2 is shown end on and the distance of separation of the two axes 4' and 6' of the respective cylinders or dowels 4,6 is D' whereas the diameter of each cylinder is D. D' is less than D. That is, the double dowel invention shown in FIGS. 1A,1B a unitized shape of two conjoined circular cylindrical dowels whose major axes are laterally spaced apart by a distance that is less than half the sum of the diameters of the two circular cylindrical dowels at all points along the major length dimension $L_M$ of the implant; and the major axes of the conjoined cylindrical dowels lie in the same plane which, when implanted within the spine of a patient, is perpendicular to the sagittal plane of the patient's spine.

An implant having the double dowel design of parallel cylinders as illustrated in FIGS. 1A,1B can be sized for use in cervical implantations. In cervical implantations the diameters D of each conjoined cylinder would be equal to one another and be in the range of 7 millimeters to 14 millimeters. The overall width of the conjoined cylinders would be less than sum of the diameters of both cylinders.

An implant having the double dowel design of parallel cylinders as illustrated in FIGS. 1A,1B can also have an overall size appropriate for use in lumbar implantations. In lumbar implantations the diameters D of each conjoined cylinder would be equal to one another and be in the range of 10 millimeters to 22 millimeters. The overall width of the conjoined cylinders would be less than sum of the diameters of both cylinders.

Conjoined Double Dowel Graft with Taper—Graft Embodiment No.2

Referring to FIG. 2A there is shown in oblique view a vertebral implant or graft 10 made of donor bone for use in the fusion of adjacent vertebral bodies. The graft has the unitized shape of two conjoined circular cylinders 14 and 16 with a lordotic tapered end portion 15. The axes of the unitized conjoined circular cylinders are parallel one another and separated by a distance such that the overall width of the two conjoined cylinders is less than the sum of the diameters of each cylinder. The diameters of each of the two circular cylinders 14, 16 are both equal to d. The specific geometry is more evident in FIGS. 2B and 2C. FIG. 2B is an orthogonal view of the implant 10 showing the parallel axes of the respective cylindrical portions 14 and 16 and one face 12 of the lordotic taper portion 15. FIG. 2C is an orthogonal view of the implant 10 from a direction perpendicular to that shown in FIG. 2B. Evident in FIG. 2C are the faces 12 of the tapered end portion 15 in relation to the major axis A"-A" of the implant. The diameters d, as shown in FIG. 2A, of each of the two circular cylinders 14,16 is greater than the separation distance d' between the axes of each circular cylinder 14, 16 shown in FIG. 2B. When implanted, the major axes of the conjoined circular cylindrical dowels lie in the same plane which is to be perpendicular to the sagittal plane of the patient's spine.

An implant having the double dowel design of parallel cylinders with a taper at one end as illustrated in FIGS. 2A, 2B and 2C can have an overall size appropriate for use in cervical implantations. In cervical implantations the diameters d of each conjoined cylindrical dowel would be equal to one another and be in the range of 7 millimeters to 14 millimeters. The overall width of the conjoined cylinders would thus be less than sum of the diameters d of both cylinders.

An implant having the double dowel design of parallel cylinders with a lordotic taper as illustrated in FIGS. 2A,2B and 2C can also have an overall size appropriate for use in lumbar implantations. In lumbar implantations the diameters d of each conjoined cylindrical dowel would be equal to one another and be in the range of 10 millimeters to 22 millimeters. The overall width of the conjoined cylinders would be less than sum of the diameters d of both cylinders. In FIG. 2C the dimension designated by $L'_M$ is represents the implant's major length.

Conjoined Double Conical Dowel Graft—Graft Embodiment No.3

Referring now to FIG. 3A there is shown in oblique view a vertebral implant or graft 30 made of donor bone for use in the fusion of adjacent vertebral bodies. The graft 30 has the unitized shape of two conjoined truncated circular cones 34 and 36 each having the same base diameter or major base diameter b and minor diameter b'. The conjoined truncated conical dowels have diameters at all points along the length of the major dimension L of the implant that are equal. In FIG. 2B the axes c-c and c'-c' of the unitized conjoined circular truncated circular cones are coplanar and convergent. The distance of separation of the respective axes varies in proportion to the instant diameters of the circular conical shapes. The distance of separation of the respective conical axes c-c and c'-c' is at all instant points along the length of the major dimension L less than the diameter of either cone at the same instant point. (The instant point is any specific location along the axis c-c or c'-c' of either circular cone or along the major axis B-B of the implant lying equidistant from, or collinear with, the line bisecting the angle defined by the converging [or diverging] axes of the truncated cones.)

FIG. 3B is an orthogonal view of the two conjoined truncated conical shapes 34,36. The separation of the conical axes at the major base end 33 is b". The separation of the conical axes at the minor base end 35 is b'". The ratio of the dimensions b to b" may or may not be the same as the ratio of the dimensions b' to b'".

The conical shapes of the respective conjoined truncated circular cones comprising the implant 30 give the implant an overall lordotic taper having a major thickness th equal to b and a minor thickness equal to b' as shown in FIG. 3C. The angle of the taper can be defined approximately as the arctan (b–b')/L, where L is the major length of the implant as shown in FIG. 3C.

When implanted, the major axes of the conjoined truncated conical dowels lie in the same plane which is to be perpendicular to the sagittal plane of the patient's spine.

An implant according to this truncated circular conical embodiment 30 of the present invention can have an overall size appropriate for use in cervical implantations. In cervical implantations the major base conical diameters b of the major base end 33 of each conjoined cylinder would be equal to one another and be in the range of 7 millimeters to 14 millimeters. The corresponding diameters b' would be such as is necessary to provide the desired lordotic angle a shown in half angle portions in FIG. 3C.

An implant according to this truncated circular conical embodiment 30 of the present invention can have an overall size appropriate for use in lumbar implantations. In lumbar implantations the major base conical diameters b of the major base end 33 of each conjoined cylinder would be equal to one another and be in the range of 10 millimeters to 22 millimeters. The corresponding diameters b' would be such as is necessary to provide the desired lordotic angle a shown in half angle portions in FIG. 3C.

Conjoined Double Dowel Graft with Differing Dowel Diameters—Graft Embodiment No.4

The inventor envisions a fourth embodiment of this double dowel graft invention. FIG. 5A shows this fourth embodiment 60 in an end-on view of the graft or implant. Two cylindrical dowels 62, 64 having respective diameters $d_1$ and $d_2$ comprise this double dowel embodiment shown in oblique view in FIG. 5B. The two dowels 64, 66 are conjoined at the region 66 marked by a dotted line in FIG. 5A. Note in FIG. 5A that the width W of this embodiment is less than the sum of the respective diameters $d_1$ and $d_2$. In FIG. 5B the dimension $L''_M$ represents the major length or dimension of the implant.

In this fourth embodiment, the dowel diameters may be the same dimension or different dimensions provided the sum of the diameters exceeds the overall width W of the conjoined dowels. Clearly this means that Embodiment No.1 is a special case of this present Embodiment No.4; that is, Embodiment No.1 represents the situation, as shown in FIG. 5A, in which the respective diameters $d_1$ and $d_2$ are equal. However, while Embodiment No.1 is, geometrically speaking, a special case of Embodiment No.4, it is important to note the special usage intended for Embodiment No.4. Specifically, as shown in FIG. 5C, Embodiment No.4 is intended for use as a graft implant in the fusion of pathologically deformed vertebral bodies 61,63 such as could be found in cases of scoliosis or degenerative disc space wherein are found unequal and uncorrectable disc space heights or vertebral body misalignments. As shown in FIG. 5C, the double dowel graft of Embodiment No.4 can be implanted in the internal disc space without the need to cut into the respective adjacent endplates 65, 67 by more than about 3 millimeters. Deeper cuts into the end plates would be necessary if the goal were to maintain the misalignment of the vertebral bodies 61 and 63 while implanting a double dowel graft having equal diameters $d_1$ and $d_2$, as in Embodiment No.1. Thus in cases where spinal fusion is to be performed on misaligned vertebral bodies for which realignment would be undesirable, the double dowel graft 60, comprised of two dowels of unequal diameters $d_1, d_2$, can be used so as not to change substantially the prior alignment of the two vertebral bodies being fused nor require extra cutting of the vertebral endplates to accommodate a dowel having a diameter that might otherwise be too large. When implanted, the major axes of the conjoined circular cylindrical dowels lie in the same plane which is to be closer to being perpendicular to the sagittal plane of the patient's spine than parallel to the sagittal plane.

Conjoined Double Dowel Graft—Graft Embodiment No.5

The inventor envisions yet a fifth embodiment of this double dowel bone graft invention in which the double dowel implant is oriented vertically within the intervertebral space. FIG. 6A is a simplified orthogonal schematic view showing, in anterior view, an upper vertebral body 72 and a lower vertebral body 74 separated by a bone graft implant 76 comprised on an upper dowel portion 77 and a lower dowel portion 79. The double dowel implant 76 is similar to the implant 2 of the Embodiment No.1 as shown in FIG. 1A; it consists of two conjoined equal diameter cylindrical dowels having parallel major axes. The implant 76 is shown in FIG. 6A as being disposed such that the plane 73 (shown edge on) defined by the parallel major axes, A,B, of each dowel is parallel to the vertical axis of the spine. The plane defined by the axis A and the axis B of the respective upper and lower circular cylindrical dowels is vertically oriented such that it is parallel to the sagittal plane of the patient's spine. When implanted, the major axes A,B of the conjoined circular cylindrical dowels lie in the same plane which is to be parallel to the sagittal plane of the patient's spine.

FIG. 6B shows in a view similar to that of FIG. 6A a variation 88 of the graft implant shown in FIG. 6A. Parallel double dowels 87 and 89 are conjoined by way of a planar bridge 88 and disposed between an upper vertebral body 82 and a lower vertebral body 84 in such an orientation that the plane 83 (shown edge on) defined by the parallel major axes of each dowel is parallel to the vertical axis of the spin, as in FIG. 6A. The components of the bone graft implant 86 shown in FIG. 6B are a single contiguous mass; that is, the dowel 87 and the dowel 89 and the planar bridge 88 separating the two dowels are all cut in a single piece of material.

When implanted, the major axes A,B of the conjoined circular cylindrical dowels lie in the same plane which is to be parallel to the sagittal plane of the patient's spine.

Vertebral Distractor Tool—Embodiment No.1

Referring now to FIG. 4A there is shown in oblique view a vertebral distractor tool 40. The vertebral distractor tool 40 has two lordotic tapers 42 disposed in lateral separation from one another. The two lordotic tapers 42 serve to guide and ease the insertion of the distractor tool 40 between two respective vertebral bodies so as to maintain separation of the vertebral bodies during the preparation of the intervertebral space and installation of the bone graft implant. A curved land 45 has a radius of curvature approximately equal to the radius of curvature of the anterior faces of vertebral bodies. Were the curved land 45 to have a larger radius of curvature, approximately greater than about 6 or 7 centimeters, then the main body 41 of the distractor 40 would potentially have excessive freedom of motion in the direction indicated by the two-headed arrow 49. Such constraint on motion contributes to the overall stability of the distractor when in use.

A cavity 44 is comprised of two parallel and overlapping circular cylindrical bores 46,48 which penetrate the main body 41 of the distractor tool 40 therethrough. The cavity 44 has a conjoined double dowel shape corresponding to the cylindrical shape of the implant graft 2 shown in FIGS. 1A,1B.

When the distractor 40 is in place with its lordotic tapers 42 between two vertebral bodies (not shown), the cavity 44 serves as a cylindrical reamer guide. A cylindrical reaming tool (not shown) can be inserted into and through one hole, 46 or 48, to cut and otherwise prepare the vertebral surfaces and cortexes most adjacent the intervertebral space so as to accommodate the types of circular cylindrical double dowel grafts described hereinabove. After the reamer tool has prepared one of the two holes or guideways for the double dowel graft implant, then it can be inserted into and through the other hole to cut the adjacent region to accommodate a double dowel graft according to the present invention. That is, the reamer cuts away appropriate cylindrical portions from the lower cortical portion of the upper vertebral body and from the upper cortical portion of the lower vertebral body so as to accommodate the types of double dowel graft implants described herein and to expose cancellous living bony tissue of the vertebral bodies so as to promote new bone growth into the intervertebral space being supported, post-operatively, by the graft design embodiments described herein.

Vertebral Distractor Tool with Insertable Reamer Guides—Embodiment No.2

A second vertebral distractor embodiment is also envisioned by the inventor for preparing an intervertebral site to receive a double dowel graft according to the present invention. This second distractor embodiment consists of two parts shown in FIGS. 4B and 4C. The first part is an outer distractor body 50 having a main body 53 housing a rectangular bore cavity 47 designed to receive the second part, a insertable reamer guide 52 of the sort shown in FIG. 4C. The insertable reamer guide 52 is a rectangular solid having within itself two parallel and overlapping circular cylindrical bores 54, 56 comprising a hole 58 having the double dowel shape described hereinabove in connection with FIG. 1A.

The outer distractor body 50 has two lordotic tapers 43 disposed in lateral separation from one another. The two lordotic tapers 43 serve to guide and ease the insertion of the outer distractor body 50 between two respective vertebral bodies so as to maintain separation of the vertebral bodies during the preparation of the intervertebral space and installation of the double dowel bone graft implant according to the present invention. A curved land 45' has a radius of curvature approximately equal to the radius of curvature of the anterior faces of vertebral bodies. Were the curved land 45' to have a larger radius of curvature, approximately greater than about 6 or 7 centimeters, then the outer distractor body 50 would potentially have excessive freedom of motion in the direction indicated by the two-headed arrow 55 shown in FIG. 4B. Constraint on motion contributes to the overall stability of the present embodiment of the two-part distractor 50 when in use.

The insertable reamer guide 52 shown in FIG. 4C consists of a rectangular solid having two overlapping circular cylindrical holes 54, 56 penetrating therethrough and comprising a double-dowel shaped hole 58. The axes of the overlapping circular cylindrical holes 54 and 56 are separated by less than the diameter of either hole, and the axes of the two holes are disposed symmetrically within the areas of the two faces of the rectangular solid to which the axes are perpendicular.

When the outer distractor body 50 is in place with its lordotic tapers 43 between two vertebral bodies, the insertable reamer guide 52 can be inserted into the rectangular cavity 47, as shown in FIG. 4C. The reamer guide 52 is then held by the outer body 50 so as to stably receive a reaming tool (not shown) which can be inserted through one hole, 54 or 56, to cut away the vertebral cortex material most adjacent, above and below, the intervertebral space. The reamer tool can then be removed from the first hole 54 or 56 and then be inserted through the other hole 56 or 54 to cut the adjacent region to accommodate a graft according to the design embodiments described herein. That is, the reamer cuts away appropriate cylindrical segments from the lower cortical portion of the upper vertebral body and from the upper cortical portion of the lower vertebral body so as to accommodate the double dowel bone graft and also to expose cancellous living bony tissue that can thence grow into the intervertebral space being supported, post-operatively, by the double dowel graft embodiments according to the present invention.

An alternative design of an insertable reamer guide is shown as item 54 in FIG. 4D. The reamer guide tool 54 has the shape of a rectangular solid with a single circular cylindrical hole 59 disposed with its axis 55 parallel to four faces of the rectangular solid and perpendicular to the other two faces of the rectangular solid. The axis 55 of the circular cylindrical hole is disposed off center of that axis 57 defined by the line connecting the centroids of the two faces or the rectangular solid to which the axis 55 of the hole 59 is perpendicular.

The reamer guide 54 is designed to be received by and held within the rectangular hole 47' shown in FIG. 4D. The off-center location of the hole 59 is such as to allow the reamer guide 54 to be used to guide a reaming tool to ream a cylindrical segment from the respective cortexes of the vertebral bodies that are to be fused. More specifically, the insertable reamer guide 54 consists of a rectangular solid having within itself a cylindrical hole 59 with an axis 55 that is perpendicular to two rectangular faces of the rectangular solid and parallel to the four other rectangular faces of the rectangular solid and located such that the axis 55 of the hole 59 is separate from an axis 57 is defined by a line passing between respective centroids of the two rectangular faces to which the axis 55 is perpendicular with the separation between the axis 55 of the hole 59 and the axis 57 being less than the radius of the hole 59. In other words, the separation S of the axis 55 of the hole 59 from the centroidal axis 57 as defined above is equal to half the distance separating the two circular cylindrical halves of the type of double dowel graft 2 exemplified in FIG. 1A.

During use, the reamer guide 54 is placed inside the rectangular hole 47' as shown in FIG. 4D while the distractor outer body 50' is in place between two vertebral bodies (not shown). After a first cylindrical hole is reamed in the respective cortical portions of the vertebral bodies being fused, the reamer is removed and the reamer guide 54 is removed from the distractor outer body 50'. The reamer guide 54 is then inverted by 180 degrees, as shown by the curved double headed arrow 51, and reinserted into the rectangular cavity 47'. The reamer guide in this second position affords guidance to the reaming tool to remove the remaining cortical material from the vertebral bodies between which a double dowel bone graft of the sort described herein is to be inserted. The double reaming operation thus creates an appropriately shaped intervertebral region that can accommodate the double dowel bone grafts, or implants, according to the present invention.

I claim:

1. An intervertebral implant comprising a unitary body having a shape, said shape having a width, said shape comprising a conjoined pair of cylinders, said pair comprising a first cylinder having a first centerline and a first radius and a second cylinder having a second centerline and a second radius, said cylinders being conjoined such that the first centerline and the second centerline are separated so as to be coplanar and such that the separation between the first centerline and the second centerline is less than the sum of the first radius and the second radius, whereby the width of the shape is less than the sum of the diameter of the first cylinder and the diameter of the second cylinder.

2. The implant of claim 1 wherein the first radius and the second radius are equal.

3. The implant of claim 1 wherein the unitary body comprises bone.

4. The implant of claim 3 wherein the bone is allograft bone.

5. The implant of claim 1 further comprising at least one taper at one end, whereby the natural lordosis of the spine is accommodated.

6. The implant of claim 1 further configured to be disposed in the saggital plane of a patient's spine.

* * * * *